(12) United States Patent
Scates et al.

(10) Patent No.: US 7,208,624 B2
(45) Date of Patent: Apr. 24, 2007

(54) PROCESS FOR PRODUCING ACETIC ACID

(75) Inventors: Mark O. Scates, Houston, TX (US);
David A. Trueba, Webster, TX (US)

(73) Assignee: Celanese International Corporation, Dallas, TX (US)

( * ) Notice: Subject to any disclaimer, the term of this patent is extended or adjusted under 35 U.S.C. 154(b) by 417 days.

(21) Appl. No.: 10/708,423

(22) Filed: Mar. 2, 2004

(65) Prior Publication Data

US 2005/0197506 A1  Sep. 8, 2005

(51) Int. Cl.
*C07C 51/42* (2006.01)
*C07C 51/12* (2006.01)

(52) U.S. Cl. ........................ 562/608; 562/519
(58) Field of Classification Search ............. 562/517, 562/519, 518, 607, 608
See application file for complete search history.

(56) References Cited

U.S. PATENT DOCUMENTS

| | | | | |
|---|---|---|---|---|
| 3,769,329 A | | 10/1973 | Paulik et al. ............... | 260/488 |
| 4,629,711 A | * | 12/1986 | Erpenbach et al. ........... | 502/24 |
| 5,001,259 A | | 3/1991 | Smith et al. ................ | 562/519 |
| 5,026,908 A | | 6/1991 | Smith et al. ................ | 562/519 |
| 5,144,068 A | | 9/1992 | Smith et al. ................ | 562/519 |
| 5,371,286 A | * | 12/1994 | Blay et al. .................. | 562/519 |
| 5,416,237 A | | 5/1995 | Aubigne et al. ............. | 562/519 |
| 5,625,095 A | | 4/1997 | Miura et al. ................ | 562/519 |
| 5,723,660 A | | 3/1998 | Morimoto et al. .......... | 562/519 |
| 5,756,836 A | | 5/1998 | Shimizu et al. ............. | 562/519 |
| 5,783,731 A | | 7/1998 | Fisher et al. ................ | 562/519 |
| 5,831,120 A | | 11/1998 | Watson et al. .............. | 562/519 |
| 6,143,930 A | | 11/2000 | Singh et al. ................ | 562/608 |
| 6,339,171 B1 | | 1/2002 | Singh et al. ................ | 562/519 |

FOREIGN PATENT DOCUMENTS

| | | |
|---|---|---|
| EP | 1 061 874 | 2/1985 |
| JP | 9-40590 | 2/1997 |
| JP | 09-235250 A | 9/1997 |

OTHER PUBLICATIONS

Derrick J. Watson, *The Cativa Process for the Production of Acetic Acid*, in Catalysis of Organic Reactions, vol. 75, pp. 369-380 (1998).
R.T. Eby & T.C. Singleton, *Methanol Carbonylation to Acetic Acid*, in Applied Industrial Catalysis, vol. 1, pp. 275-296 (1983).

* cited by examiner

*Primary Examiner*—Thurman K. Page
*Assistant Examiner*—Karl J. Puttlitz
(74) *Attorney, Agent, or Firm*—Howrey LLP

(57) ABSTRACT

An improved process is disclosed for producing acetic acid, including the following steps: reacting a carbonylatable reactant such as methanol, methyl acetate, methyl formate or dimethyl ether with carbon monoxide in a reaction medium containing water, methyl iodide, and a catalyst to produce a reaction product that contains acetic acid; separating the reaction product to provide a volatile phase containing acetic acid, water, and methyl iodide and a less volatile phase; distilling the volatile phase to produce a purified acetic acid product and a first overhead containing water, methyl acetate, and methyl iodide; phase separating the first overhead to provide a first liquid phase containing water and a second liquid phase containing methyl iodide; and adding dimethyl ether to the process in an amount effective to enhance separation of the first overhead to form the first and second liquid phases.

14 Claims, 1 Drawing Sheet

PROCESS FOR PRODUCING ACETIC ACID

BACKGROUND OF INVENTION

1. Field of the Invention

This invention relates to an improved process for producing acetic acid by carbonylation of methanol.

2. Technical Background

Among currently employed processes for synthesizing acetic acid, one of the most useful commercially is the catalyzed carbonylation of methanol with carbon monoxide as taught in U.S. Pat. No. 3,769,329 issued to Paulik et al. on Oct. 30, 1973. The carbonylation catalyst contains rhodium, either dissolved or otherwise dispersed in a liquid reaction medium or supported on an inert solid, along with a halogen-containing catalyst promoter such as methyl iodide. The rhodium can be introduced into the reaction system in any of many forms, and the exact nature of the rhodium moiety within the active catalyst complex is uncertain. Likewise, the nature of the halide promoter is not critical. The patentees disclose a very large number of suitable promoters, most of which are organic iodides. Most typically and usefully, the reaction is conducted by continuously bubbling carbon monoxide gas through a liquid reaction medium in which the catalyst is dissolved.

A major improvement in the prior art process for the carbonylation of an alcohol to produce the carboxylic acid having one carbon atom more than the alcohol in the presence of a rhodium catalyst is disclosed in U.S. Pat. No. 5,001,259 (issued Mar. 19, 1991); U.S. Pat. No. 5,026,908 (issued Jun. 25, 1991); and U.S. Pat. No. 5,144,068 (issued Sep. 1, 1992) and European Patent No. EP 0 161 874 B2, published Jul. 1, 1992. These patents disclose a process in which acetic acid is produced from methanol in a reaction medium containing methyl acetate, methyl halide, especially methyl iodide, and a catalytically effective concentration of rhodium. The inventors of these patents discovered that catalyst stability and the productivity of the carbonylation reactor can be maintained at surprisingly high levels, even at very low water concentrations, i.e. 4 weight (wt) % or less, in the reaction medium (despite the general industrial practice of maintaining approximately 14 wt % or 15 wt % water) by maintaining in the reaction medium, along with a catalytically effective amount of rhodium, at least a finite concentration of water, methyl acetate and methyl iodide, a specified concentration of iodide ions over and above the iodide content that is present as methyl iodide or other organic iodide. The iodide ion is present as a simple salt, with lithium iodide being preferred. The patents teach that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %, so low that it can be defined simply as "a finite concentration" of water. Furthermore, the reaction medium employed improves the stability of the rhodium catalyst, i.e. its resistance to catalyst precipitation, especially during the product recovery steps of the process. Distillations carried out in the process to recover the acetic acid product tend to remove carbon monoxide ligands from the catalyst. These ligands have a stabilizing effect on the rhodium in the environment maintained in the reaction vessel. U.S. Pat. Nos. 5,001,259, 5,026,908 and 5,144,068 are incorporated herein by reference.

It has also been found that although a low water carbonylation process for the production of acetic acid reduces such by-products as carbon dioxide, hydrogen, and propionic acid, the amount of other impurities, present generally in trace amounts, is also increased, and the quality of acetic acid sometimes suffers when attempts are made to increase the production rate by improving catalysts, or modifying reaction conditions. These trace impurities affect the quality of the acetic acid product, especially when they are recirculated through the reaction process. See *Catalysis of Organic Reactions*, 75, 369–380 (1998), for further discussion on impurities in a carbonylation reaction system.

The crude acetic acid product is typically distilled in one or more distillation columns to remove light ends reaction components (typically methyl acetate and methyl iodide), water and heavy ends impurities. It has previously been observed that it is particularly important to avoid refluxing large amounts of methyl iodide back into the light ends distillation column because the separation of light ends reaction components from acetic acid product is significantly degraded if methyl iodide is allowed to reflux back into the light ends column. Ordinarily the refluxing of methyl iodide is prevented by separating most of the methyl iodide from the light ends overhead as a distinct phase, but under certain conditions the light ends overhead can form a single liquid phase that includes methyl iodide. The present invention provides one method of preventing this single-phase condition in the light ends column overhead.

SUMMARY OF INVENTION

One aspect of the present invention is a process for producing acetic acid, which includes the following steps: reacting carbon monoxide with a carbonylatable material such as methanol, methyl acetate, methyl formate, dimethyl ether, or mixtures thereof, in a reaction medium containing water, methyl iodide, and a catalyst to produce a reaction product that contains acetic acid; performing a vapor-liquid separation on the reaction product to provide a volatile phase containing acetic acid, water, and methyl iodide and a less volatile phase containing the catalyst; distilling the volatile phase to produce a purified acetic acid product and a first overhead containing water and methyl iodide; phase separating the first overhead to provide a first liquid phase containing water and a second liquid phase containing methyl iodide; and adding dimethyl ether to the process in an amount effective to enhance separation of the first overhead to form the first and second liquid phases.

Another aspect of the invention is an improved method for distilling a mixture containing acetic acid, methyl iodide, and water to provide a purified acetic acid product, a first liquid phase containing water, and a second liquid phase containing methyl iodide. In this method, an overhead fraction in the distillation is separated to form the first and second liquid phases, and a portion of the first liquid phase is refluxed in the distillation. The improvement involves adding dimethyl ether to the mixture, to the overhead fraction or to the refluxed portion of the first liquid phase in an amount effective to enhance phase separation of the first and second liquid phases.

Figure 1:
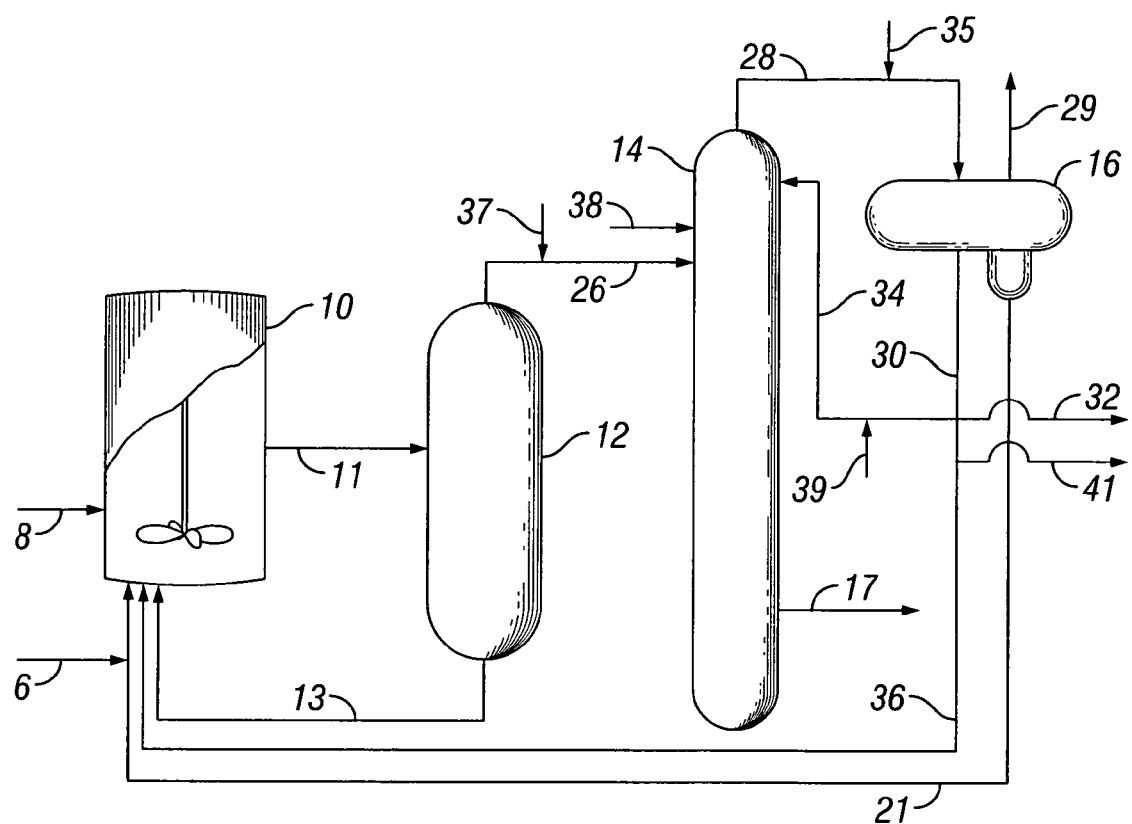
FIG. 1 is a process flow diagram for a process according to the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is intended to cover all modifications, equivalents and alternatives falling within the scope of the invention as defined by the appended claims.

DETAILED DESCRIPTION

An illustrative embodiment of the invention is described below. In the interest of clarity, not all features of an actual implementation are described in this specification. It will of course be appreciated that in the development of any such actual embodiment, numerous implementation-specific decisions must be made to achieve the developers" specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention is useful in any process used to carbonylate methanol to acetic acid in the presence of a Group VIII metal catalyst such as rhodium and an iodide promoter. A particularly useful process is the low water rhodium-catalyzed carbonylation of methanol to acetic acid as exemplified in the aforementioned U.S. Pat. No. 5,001,259. The rhodium component of the catalyst system may be provided by introducing rhodium into the reaction zone in the form of rhodium metal, rhodium salts such as oxides, acetates, iodides, etc., or other coordination compounds of rhodium.

The halogen-promoting component of the catalyst system includes an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol, which is carbonylated. Thus, in the carbonylation of methanol to acetic acid, the halide promoter will be a methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process is the carboxylic acid product itself. Thus, in the carbonylation of methanol to acetic acid, the preferred solvent is acetic acid.

Water is present in the reaction medium at concentrations well below that which had originally been thought practical for achieving sufficient reaction rates. It had previously been taught that in rhodium-catalyzed carbonylation reactions of the type set forth in this invention, the addition of water exerts a beneficial effect upon the reaction rate (U.S. Pat. No. 3,769,329). Thus most commercial operations run at water concentrations of at least about 14 wt %. Accordingly, it was quite unexpected that reaction rates substantially equal to and above reaction rates obtained with such high levels of water concentration could be achieved with water concentrations below 14 wt % and as low as about 0.1 wt %.

In accordance with the carbonylation process most useful to manufacture acetic acid according to the present invention, the desired reaction rates are obtained even at low water concentrations by including in the reaction medium methyl acetate and an additional iodide ion which is over and above the iodide which is present as a catalyst promoter such as methyl iodide or other organic iodide. The additional iodide promoter is an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously (U.S. Pat. No. 5,001,259).

The carbonylation reaction of methanol to acetic acid product may be carried out by contacting the methanol feed, which is typically in the liquid phase, with gaseous carbon monoxide bubbled through a liquid acetic acid solvent reaction medium containing the rhodium catalyst, methyl iodide promoter, methyl acetate, and additional soluble iodide salt, at a temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Consequently, any metal iodide salt, or any iodide salt of any organic cation, or quaternary cation such as a quaternary amine or phosphine or inorganic cation can be used provided that the salt is sufficiently soluble in the reaction medium to provide the desired level of the iodide. When the iodide is added as a metal salt, preferably it is an iodide salt of a member of the group consisting of the metals of Group IA and Group IIA of the periodic table as set forth in the Handbook of Chemistry and Physics published by CRC Press, Cleveland, Ohio, 2002–03 (83rd edition). In particular, alkali metal iodides are useful, with lithium iodide being preferred. In the low water carbonylation process most useful in this invention, the additional iodide over and above the organic iodide promoter is present in the catalyst solution at about 2 to about 20 wt %, the methyl acetate is present at about 0.5 to about 30 wt %, and the lithium iodide is present at about 5 to about 20 wt %. The rhodium catalyst is present at about 200 to about 2000 parts per million by weight (ppm).

Typical reaction temperatures for carbonylation are about 1500 to about 250° C., preferably about 1800 to about 220° C. The carbon monoxide partial pressure in the reactor can vary widely but is typically about 2 to about 30 atmospheres, and preferably about 3 to about 10 atmospheres. Because of the partial pressure of by-products and the vapor pressure of the contained liquids, the total reactor pressure will range from about 15 to about 40 atmospheres.

A typical reaction and acetic acid recovery system used for the iodide-promoted rhodium catalyzed carbonylation of methanol to acetic acid is shown in FIG. 1. The reaction system includes a carbonylation reactor 10, a flasher 12, and a methyl iodide/acetic acid light ends column 14 which has an acetic acid side stream 17 which proceeds to further purification. As disclosed in U.S. Pat. No. 5,416,237, incorporated herein by reference, light ends column 14 may also incorporate additional stages that facilitate the separation of acetic acid and water, thus obviating the need for a separate drying column to accomplish this separation. The carbonylation reactor 10 is typically a stirred vessel or bubble-column type within which the reacting liquid contents are maintained automatically at a constant level. Into this reactor there are continuously introduced fresh methanol via stream 6, carbon monoxide via stream 8, sufficient water as needed to maintain at least a finite concentration of water in the reaction medium, recycled catalyst solution via stream 13 from the base of flasher 12, a recycled methyl iodide and methyl acetate phase 21, and a recycled aqueous acetic acid phase 36 from an overhead receiver decanter of the methyl iodide acetic acid light ends or splitter column 14. Distillation systems are employed that provide for recovering the crude acetic acid and recycling catalyst solution, methyl iodide, and methyl acetate to the reactor. In one preferred process, carbon monoxide is continuously introduced into a stirred carbonylation reactor just below the agitator, thereby thoroughly dispersing the carbon monoxide through the reacting liquid. A gaseous purge stream is vented from the reactor to prevent buildup of gaseous by-products and to control the partial pressure of carbon monoxide at a given total reactor pressure. The temperature of the reactor is controlled and the carbon monoxide feed is introduced at a rate sufficient to maintain the desired total reactor pressure.

Liquid product is drawn off from the carbonylation reactor 10 at a rate sufficient to maintain a constant level therein and is introduced to the flasher 12. In the flasher the catalyst solution is withdrawn as a base stream (predominantly acetic acid containing the rhodium catalyst and the iodide salt along with lesser quantities of methyl acetate, methyl iodide, and water), while the vapor overhead stream of the flasher contains the crude acetic acid product along with some methyl iodide, methyl acetate, and water. The stream 11 exiting the reactor and entering the flasher also contains dissolved gases including a portion of the carbon monoxide along with gaseous by-products such as methane, hydrogen, and carbon dioxide. These exit the flasher as part of the vapor overhead stream 26 that is directed to the light ends or splitter column 14.

From the top of the light ends or splitter column 14, vapors are removed via stream 28, condensed, and directed to decanter 16. Stream 28 contains condensable water, methyl iodide, methyl acetate, acetaldehyde and other carbonyl components, as well as noncondensable gases such as carbon dioxide, hydrogen, and the like that can be vented as shown in stream 29 on FIG. 1. The condensable vapors are preferably cooled to a temperature sufficient to condense and separate the condensable methyl iodide, methyl acetate, acetaldehyde and other carbonyl components, and water into two liquid phases. At least a portion of stream 30 is directed back to the light ends column 14 as reflux stream 34; in a preferred embodiment of the invention, another portion of stream 30 is diverted as side stream 32 and is processed to remove acetaldehyde and other permanganate reducing compounds before being returned to the reaction system or the light ends column. A number of treatment methods are known in the art for removing acetaldehyde and other PRes; examples of such methods are disclosed in U.S. Pat. Nos. 5,625,095; 5,783,731; 6,143,930; and 6,339,171, each of which is incorporated herein by reference in its entirety. To help maintain the water balance within the process, still another portion 41 of the light phase 30 may be purged from the system or treated to remove excess water before being returned to the reaction system.

The heavy phase 21 of stream 28 leaving overhead receiver decanter 16 is ordinarily recirculated to the reactor, but a slip stream, generally a small amount, e.g., 25 volume %, preferably less than about 20 volume % of the heavy phase may also be directed to a PRe removal process and the remainder recycled to the reactor or reaction system. This slip stream of the heavy phase may be treated individually, or combined with the light phase, stream 30 for further distillation and extraction of carbonyl impurities.

As has been previously explained, it is highly desirable to maintain a low concentration of water, for example below 8 percent and preferably much lower, in the carbonylation reaction medium for at least two reasons: first, maintaining a low water concentration helps to control the amount of carbon dioxide formed as a by-product in the reactor by the water gas shift reaction. Second, and more significantly, low water concentrations also help to control the amount of propionic acid formed as a by-product. As the water concentration in the reaction medium is lowered, however, the vapor load on column 14 increases. This increased vapor load results in unacceptably high carryover of acetic acid into the decanter 16 at the top of the light ends column 14. The solubility of acetic acid in both the methyl iodide and aqueous phases causes phase separation to deteriorate, eventually resulting in a single liquid phase in the decanter. When this condition occurs, the reflux to column 14 includes a high concentration of methyl iodide. The presence of this additional methyl iodide significantly interferes with the ability of column 14 to cleanly separate light ends materials such as methyl acetate from the acetic acid product 17. This frequently requires that the entire reaction system be shut down until the problem can be corrected. (For this reason, only the light phase 30, which has relatively little methyl iodide, is typically used as reflux in column 14.) In view of this potential problem, it is extremely important to maintain phase separation in the decanter 16, even though this is made more difficult by the low-water reaction conditions and by the tendency of high concentrations of methyl acetate to create high vapor loads in the light ends column, which promotes the formation of a single phase as mentioned above. Although this problem has been recognized to some extent in U.S. Pat. No. 5,723,660, the disclosure of which is incorporated herein by reference, the solutions proposed therein involve expensive steps such as distilling the light ends overhead to remove methyl acetate or significantly reducing the temperature to which the light ends overhead is cooled before it enters the decanter. The third proposed solution, feeding water batchwise into the light ends column to ensure that the methyl acetate concentration remains below 40 weight percent, is likely to significantly alter the water balance throughout the process each time water is added.

The present applicants have discovered another effective method of ensuring phase separation in the light ends overhead decanter 16 without any of the complicated steps proposed in the U.S. Pat. No. 5,723,660 and without significantly altering the water balance in the process. In simple terms, the applicants have discovered that proper phase separation in the decanter can be ensured by adding a component that (a) is immiscible in water; (b) is compatible with the process chemistry and (c) counteracts the effect of acetic acid in promoting a single phase. Specifically, the applicants have found that by adding dimethyl ether (DME) to the light ends overhead, the light ends column feed, or another stream associated with the light ends column 14, the liquid contents of decanter 16 can be prevented from forming a single phase.

In addition to being nearly immiscible with water, DME is compatible with the process chemistry. As explained above, the organic (methyl iodide-rich) heavy phase formed in decanter 16 is returned to the carbonylation reactor 10. DME reacts with water and carbon monoxide under carbonylation reaction conditions to produce acetic acid. Moreover, as has been disclosed in U.S. Pat. No. 5,831,120, because the carbonylation of DME consumes water, DME is also useful for controlling the accumulation of water in the process. For example, the additional water consumed in the carbonylation of DME may make it unnecessary to purge or treat the portion 36 of light phase 30 that returns to the reactor to remove excess water. Finally, the presence of DME in the side stream 32 of light phase 30 that is further processed to remove acetaldehyde has certain beneficial effects. Most notably, as disclosed in more detail in commonly assigned U.S. patent application Ser. Nos. 10/708,420 and 10/708,421, filed concurrently herewith, when sufficient DME is present in the light phase side stream 32 or formed in situ in the acetaldehyde removal system, undesirable losses of methyl iodide during the acetaldehyde removal process are significantly reduced.

It will be appreciated that in acetic acid processes such as the process described above, a number of process streams are recycled within the purification area or from the purification area to the reaction system. Consequently, DME may be added anywhere in the process provided that a sufficient quantity of DME accumulates in the light ends decanter 16 to achieve the desired effect of enhancing phase separation therein. For example, DME may be injected (via stream 37) into the flasher overhead 26 that feeds the light ends column 14 or may be separately fed to the column (via stream 38). Alternatively, DME may be injected into the light ends column via reflux stream 34. It is presently believed, however, that feeding additional DME through the light ends column 14 may contribute excessively to the vapor load in the column. Accordingly, it is preferred to add DME directly or indirectly to the light ends decanter 16 via a stream or series of streams that does not pass through the light ends column 14. For example, DME may be added directly to light ends overhead stream 28 (as stream 35). Alternatively, in certain embodiments of the acetaldehyde removal technology disclosed in U.S. Pat. No. 6,143,930 and in co-pending U.S. patent application Ser. Nos. 10/708,420 and 10/708,421, both filed on Mar. 2, 2004, all or a portion of the return stream from the acetaldehyde removal system returns to the decanter 16 or light ends column 14. DME could be added to such a return stream as well (e.g., stream 46 in FIG. 1 of U.S. Pat. No. 6,143,930) or to a stream elsewhere within the acetaldehyde removal system such that the return stream contains sufficient DME to enhance phase separation in decanter 16.

While the invention has been described with reference to the preferred embodiments, obvious modifications and alterations are possible by those skilled in the art. Therefore, it is intended that the invention include all such modifications and alterations to the full extent that they come within the scope of the following claims or the equivalents thereof.

The invention claimed is:

1. A process for producing acetic acid, comprising the steps of:
    (a) reacting carbon monoxide with at least one reactant selected from the group consisting of methanol, methyl acetate, methyl formate, dimethyl ether and mixtures thereof in a reaction medium comprising water, methyl iodide, and a catalyst to produce a reaction product comprising acetic acid;
    (b) performing a vapor-liquid separation on said reaction product to provide a volatile phase comprising acetic acid, water, and methyl iodide and a less volatile phase comprising said catalyst;
    (c) distilling said volatile phase to produce a purified acetic acid product and a first overhead comprising water, methyl acetate, and methyl iodide;
    (d) phase separating said first overhead to provide a first liquid phase comprising water and a second liquid phase comprising methyl iodide; and
    (e) adding dimethyl ether to the process in an amount effective to enhance separation of the first overhead to form the first and second liquid phases.

2. A process according to claim 1, wherein the dimethyl ether is added to at least one of said reaction product, said volatile phase, said first overhead, or a stream or column associated with said distillation.

3. A process according to claim 2, wherein the dimethyl ether is added to said first overhead.

4. A process according to claim 1, further comprising the step of removing acetaldehyde from at least one of said first and second liquid phases, and wherein the dimethyl ether is added to a stream associated with the acetaldehyde removal step.

5. A process according to claim 4, wherein the dimethyl ether is added to a return stream from an acetaldehyde removal system.

6. A process according to claim 4, wherein the step of removing acetaldehyde comprises extracting the acetaldehyde from a mixture comprising methyl iodide, and wherein a portion of the dimethyl ether is effective to reduce the quantity of methyl iodide extracted from said mixture with the acetaldehyde.

7. A process according to claim 1, wherein at least a portion of the first liquid phase is employed as a reflux stream in the distillation of the volatile phase.

8. A process according to claim 1, wherein the second liquid phase is recycled to provide a portion of the reaction medium.

9. A process according to claim 8, wherein a majority of the added dimethyl ether is recycled into the reaction medium in the second liquid phase.

10. A process according to claim 9, wherein at least some of the recycled dimethyl ether is converted to acetic acid in the reaction medium.

11. In a method for phase separating a mixture comprising acetic acid, methyl acetate, methyl iodide, and water to provide a first liquid phase comprising water and methyl acetate and a second liquid phase comprising methyl iodide, the improvement comprising adding dimethyl ether to the mixture to facilitate the separation.

12. A method for separating a mixture comprising acetic acid, methyl iodide, and water to provide a purified acetic acid product, a first liquid phase comprising water, and a second liquid phase comprising methyl iodide, comprising the steps of:
    distilling the mixture to provide an overhead fraction and said purified acetic acid product;
    phase separating the overhead fraction to provide said first and second liquid phases;
    refluxing a portion of the first liquid phase in the distillation; and
    adding dimethyl ether to the mixture, to the overhead fraction or to the refluxed portion of the first liquid phase in an amount effective to enhance phase separation of the first and second liquid phases.

13. The method of claim 12, wherein the dimethyl ether is added to the overhead fraction.

14. The method of claim 12, wherein the mixture is provided as a volatile phase of a reaction product of a carbonylation reactor.

* * * * *